United States Patent [19]

Santus et al.

[11] Patent Number: 5,674,533
[45] Date of Patent: Oct. 7, 1997

[54] PHARMACEUTICAL COMPOSITION FOR THE CONTROLLED RELEASE OF MOGUISTEINE IN A LIQUID SUSPENSION

[75] Inventors: Giancarlo Santus, Milan; Ettore Bilato, Padua; Gabriele Lazzarini, Pero, all of Italy

[73] Assignee: Recordati, S.A., Chemical And Pharmaceutical Company, Chiasso, Switzerland

[21] Appl. No.: 452,435

[22] Filed: May 26, 1995

[30] Foreign Application Priority Data

Jul. 7, 1994 [IT] Italy ............... MI94A1410

[51] Int. Cl.⁶ .................................................. A61K 9/16
[52] U.S. Cl. ........................... 424/493; 424/494; 424/498
[58] Field of Search ........................... 514/367; 424/493, 424/494, 498

[56] References Cited

U.S. PATENT DOCUMENTS

| | | | |
|---|---|---|---|
| 5,206,254 | 4/1993 | Gandolfi et al. | 514/365 |
| 5,296,236 | 3/1994 | Santus et al. | 424/490 |
| 5,460,828 | 10/1995 | Santus et al. | 424/489 |

FOREIGN PATENT DOCUMENTS

| | | | |
|---|---|---|---|
| 0169581A2 | 7/1985 | European Pat. Off. | C07D 277/04 |
| 0359195 | 3/1990 | European Pat. Off. | A61K 9/54 |

OTHER PUBLICATIONS

Chemical Abstracts 121 (7), abstract No. 73498, Aug. 15, 1994.
Gallico, L., et al., (1994), Br. J. Pharmacol., 112(3):795–800. Abstract.
Jones, David, (1994), *Drug Development and Industrial Pharmacy*, 20(20):3175–3206.
Sampson, S. R., et al., (1979), *Adv.Exp. Med. Biol.*, 281–290.
Castoldi, D., et al., (1990), *Pharmacological Research*, 22:102.
Cramer, Joyce A., et al., (1989), *JAMA ed. it.*, 261(22):3273–3277.
De Angelis, L., (1991, *Drugs of the Future*, 16(7):618–619.
Jozwiakowski, Michael, et al., (1990), *Pharmaceutical Research*, 7(11):1119–1126.
Wells, James I., (1988), *Pharmaceutical Preformulation*, 209–214.
Neumann, Barbara S., (1967), *Advances in Pharmaceutical Science.*, 181–221.

Primary Examiner—Jeffrey Mullis
Attorney, Agent, or Firm—Darby & Darby

[57] ABSTRACT

Disclosed are compositions and dosage forms containing moguisteine and having controlled release properties, methods for using such compositions and dosage forms and methods for making them.

34 Claims, 2 Drawing Sheets

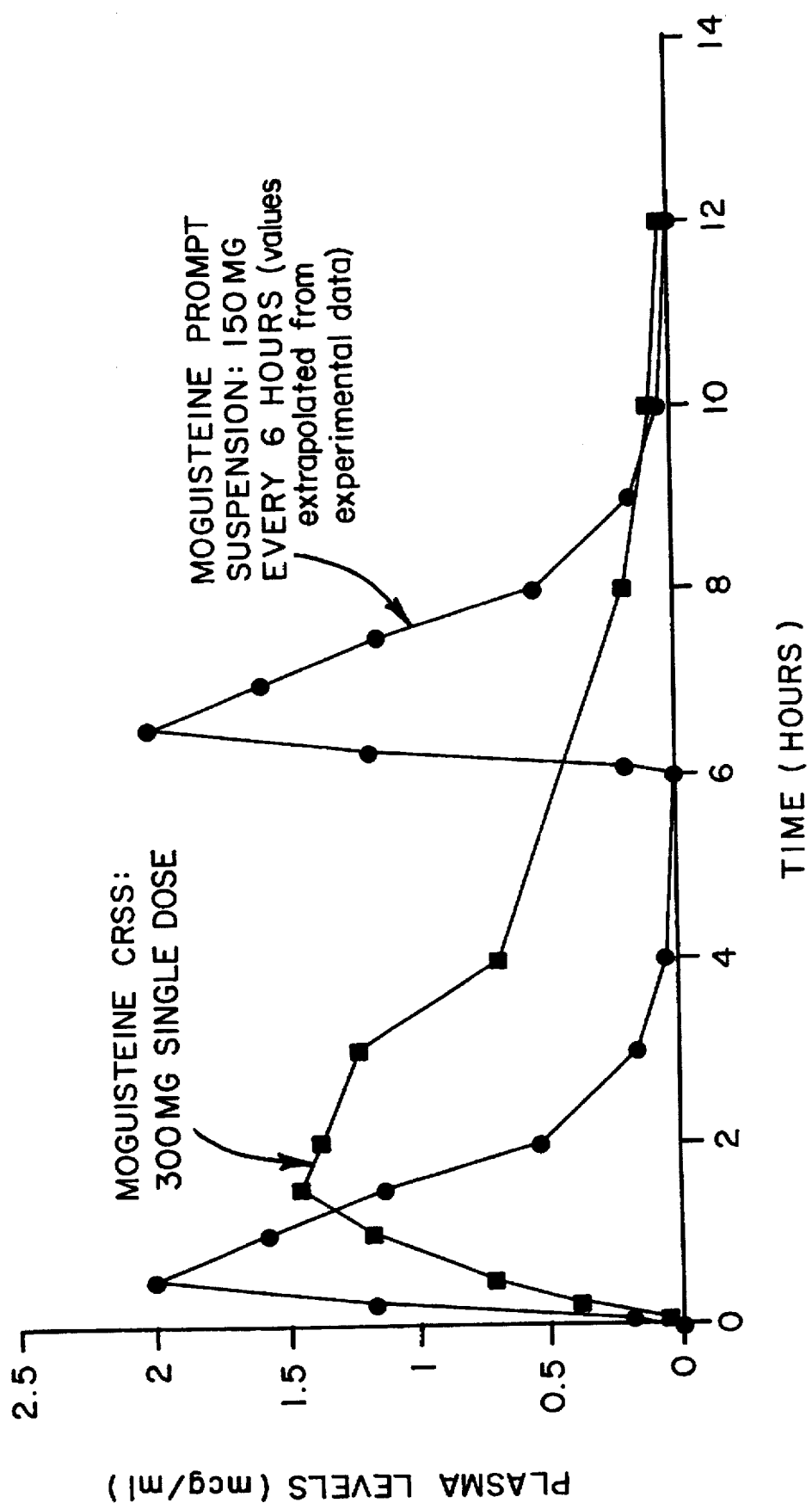

PHARMACEUTICAL COMPOSITION FOR THE CONTROLLED RELEASE OF MOGUISTEINE IN A LIQUID SUSPENSION

FIELD OF THE INVENTION

This invention involves controlled-release pharmaceutical compositions in liquid dosage forms for the administration of moguisteine.

BACKGROUND OF THE INVENTION

Moguisteine, (R.S)-2-[(2-methoxyphenoxy)methyl-3-ethoxycarbonyl-1-acetyl]-1,3-thiazolidine, is a potent peripheral antitussive described in European patent EP 169,581.

Coughing may be pharmacologically relieved by either suppressing the neuronal coughing reflex or by reducing the amount or viscosity of fluids in the respiratory tract. Some antitussives of the first type, termed "meconic agents," act by centrally depressing coughing centers. Codeine, one example of a meconic agent, is the most widely used antitussive, but has the disadvantage of potentially causing addiction. Thus, there is a need in the art for non-narcotic antitussives.

Moguisteine is an antitussive that is as potent as codeine, dextromethorphan and zipripol, and 3–4 times more potent than (D,L)-dropropizine. Importantly, it causes no addiction, and is better tolerated in high doses than codeine or dextromethorphan as it induces sedation and a reduced lower tonus. Moguisteine is a racemic mixture of R(+) and S(−) enantiomers that have equivalent antitussive activity.

Studies on the mechanism of action of moguisteine have shown that moguisteine does not act via opioid receptors. Its site of action is peripheral, and it interacts with the so-called "rapidly adapting irritant receptors" (RARs) (Sampson, S. R., et al., *Adv. Exp. Med. Biol.* 99:281–290, 1979).

Moguisteine has the characteristics of a prodrug. After oral or intravenous administration, only its active metabolite, (R,S)-2-[(methoxyphenoxy)methyl]-3-carboxyacetyl]-1,3 thiazolidine acid, can be found in biological fluids in measurable quantities. This active metabolite, however, is not suitable for oral administration because it is absorbed at a rate five times slower than moguisteine.

The moguisteine oral formulations known so far include tablets and packages for 200-mg doses and a conventional 2% suspension. The daily dose ranges from 100 to 800 mg, with the lower dosages being administered to children.

One limitation on the use of moguisteine is its short half-life after administration, which, in humans, is less than one hour. Prior to the present invention, this meant that frequent administration, i.e., at least three to four times a day, was necessary to maintain constant therapeutic blood levels (Castoldi D. et al., (1990). *Pharmacol. Res.*, 22:102).

It is known that a requirement for multiple daily administrations adversely affects patient compliance. Average compliance for drugs taken once a day is 87% but drops to 39% for drugs taken four times a day; therefore, formulations that can be administered twice daily or, even better, as a single daily dose, are significantly preferred (Kramer, J. A. et al., (1989), *JAMA*, 1:601.)

A reduction in the number of doses can be achieved using slow-release dosage forms such as tablets, pellets or the like. For antitussive formulations, however, liquid formulations are the preferred dosage forms.

U.S. Pat. No. 5,296,236 (hereinafter, the "'236 patent") describes controlled-release pharmaceutical compositions for liquid formulations, which comprise microgranules coated with several polymeric layers. In some of these compositions, a fraction of the active ingredient in the formulation is made available over time by release from the microgranules, whereas a fraction is present in the extragranular ingredients and is bioavailable immediately after administration. The compositions described in the '236 patent, however, offer a suboptimal solution to particular problems raised by liquid administration of moguisteine.

A first consideration is the very unpleasant taste of moguisteine. This makes the use of suspension formulations or solutions undesirable; thus, it is not possible to include immediately bioavailable extragranular moguisteine as in the '236 patent.

In order to obtain a moguisteine formulation that can be easily suspended, the size of the microgranules after coating must be smaller than 500 µm. Granules with sizes larger than 500 µm cannot be easily suspended as they tend to rapidly sediment, causing a non-homogeneous distribution of the active ingredient on administration. Using microgranular particles smaller than 500 µm, however, increases the surface area considerably, making it more difficult, as compared to tablets or pellets, to control release of the active ingredient and maintain it unchanged in time after reconstitution of the suspension. The difficulty is even greater when, as in the case of moguisteine, the lack of extragranular drug increases the diffusion gradient and speeds release of the drug from the granules to the surrounding milieu.

A second consideration in designing an appropriate dosage form for moguisteine using the teachings of the '236 patent is the relatively low melting point of the molecule, i.e., about 65° C. (*Drugs of the Future*, (1991), 16:618). The problem arises because waxy lipophilic materials such as white beeswax, cetyl alcohol, stearyl alcohol, glyceryl monostearate and the like (the use of which as coating materials is taught in the '236 patent), are particularly advantageous for coating moguisteine-containing microgranules so as to effectively mask their bitter taste. These materials can either be solubilized and applied using chlorinated solvents, which presents toxicological and environmental problems, or they can be applied to microgranules in the melted state (*Pharm. Res.*, (1990), 7:1119.) The use of chlorinated solvents, however, presents toxicological and environmental problems. The latter approach necessitates the use of heated compressed air to maintain the wax at a temperature above its melting point, since at lower temperatures waxes tend to solidify and are thus no longer usable as filming material. The use of relatively high temperatures, however, can liquify low-melting active ingredients such as moguisteine and thus cause the coating procedure to fail, leaving the use of chlorinated solvents (with its disadvantages) as the only alternative.

In summary, in the case of moguisteine and drugs with similar properties, there is a need for controlled-release liquid formulations that:

1) are easy to measure and to ingest;
2) have a time-dependent release that offsets the short half-life of the active ingredient and thus do not require multiple dosages;
3) exhibit satisfactory stability after suspension in a liquid vehicle;
4) are sufficiently palatable to ensure patient compliance; and
5) do not require the use of chlorinated solvents or other environmentally undesirable or toxic materials.

It is thus an object of the present invention to provide a controlled-release pharmaceutical composition, in a liquid suspension, capable of ensuring therapeutically active blood levels of moguisteine (or, more accurately, its biologically active metabolites) by one or two daily administrations. Preferably, the composition is characterized by excellent palatability and good stability with time after reconstitution with water.

It is a further object of the invention to provide a pharmaceutical composition comprising microgranules containing moguisteine that are coated with at lease three successive film layers that protect the moguisteine from dissolution in the oral cavity (or upon reconstitution in a suspension) and promote its release in distal parts of the gastrointestinal tract.

It is still a further object of the invention to provide a method for coating microgranules containing low melting-point active ingredients such as moguisteine with waxes, while avoiding either melting the active ingredient or using chlorinated solvents.

SUMMARY OF THE INVENTION

It has now been found that a controlled-release pharmaceutical dosage form suitable for the administration of moguisteine in a liquid suspension can be achieved using a multiplicity of microgranules containing moguisteine as an active ingredient, which are coated with a succession of at least three coating layers comprising alternating hydrophilic and lipophilic films and which are then formulated in a pharmaceutically acceptable vehicle. The microgranular core, in addition to moguisteine, may contain at least one plasticizer, preferably polyethylene glycol, as well as other, optional, excipients, and have sizes from 50 to 500 μm and smooth surfaces suitable for coating with polymeric or waxy materials. The coatings prevent release of moguisteine in the oral cavity and ensure a subsequent predetermined release profile of moguisteine in distal parts of the gastrointestinal tract and maintenance of the release profile over time. At least one of the coatings should impart control release characteristics to the moguisteine-containing composition. Optionally, the vehicle may comprise one or more of suspending, structuring, surfactant, sweetening, buffering, preserving and flavoring agents, as is within the skill in the art. The dosage form may be formulated as a liquid suspension in water (or in a mixture of water and water-miscible co-solvents) or as a dry powder to be reconstituted with water and/or other solvents at the time of use.

In a preferred embodiment, microgranules containing moguisteine and polyethylene glycol in a proportion of 0.5-1% by weight of the mixture receive one or two coatings comprising cellulose acetate phthalate alternating with one or two coatings comprising a waxy material such as, for example, mono-, di- and tri-glycerides of $C_6$–$C_{36}$ fatty acids, carnauba wax, beeswax, candelilla wax, alcohols, fatty acids, or combinations of the foregoing. Preferably, the waxy coating(s) is (are) applied in the melted state (i.e., without the use of solvents), by using heated compressed air as a spray medium under conditions that do not melt the microgranular core.

The moguisteine formulations of the present invention not only exhibit controlled-release characteristics that reduce the number of administrations required to maintain consistent blood levels of moguisteine, but also display excellent palatability and stability upon reconstitution as a suspension. This is due to the fact that the active ingredient remains incorporated within the coated microgranulate immediately following ingestion, and thus passes easily and quickly through the upper digestive tract without being tasted.

In another aspect, the present invention encompasses a method for symptomatic treatment of coughing, which comprises administering effective amounts for treating coughing of the dosage form described above.

In yet another aspect, the present invention provides a method for preparing a palatable controlled-release pharmaceutical dosage form for the administration of moguisteine in a liquid suspension, which involves coating the moguisteine-containing microgranules with the waxy materials in their melted state, using heated compressed air as a spray medium. The method is applicable to coating any microgranules containing any pharmaceutically active ingredient, but is particularly applicable to microgranules containing a low-melting active ingredient.

BRIEF DESCRIPTION OF THE DRAWINGS

FIG. 2 is a graph illustrating a simulation of the blood levels of moguisteine that would result after two administrations of a standard suspension of moguisteine or a single administration of the controlled-release moguisteine formulation of the present invention.

DETAILED DESCRIPTION OF THE INVENTION

Figure 1:
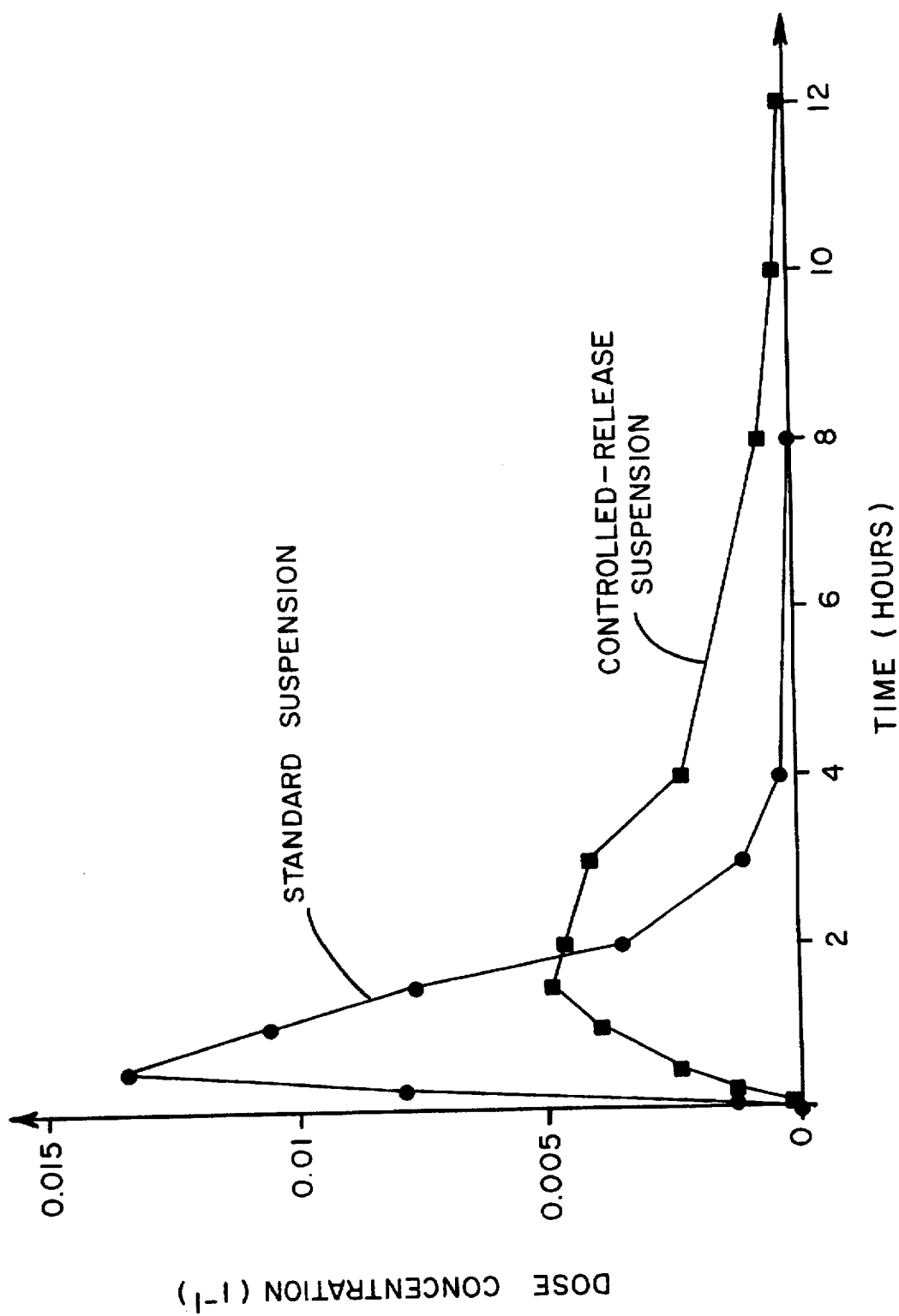
FIG. 1 is a graph illustrating the concentrations of moguisteine in the plasma of patients administered either a standard suspension, or the controlled-release formulation of the present invention.

All patents, patent applications, and literature references referred to herein are hereby incorporated by reference in their entirety. In the case of inconsistencies, the present specification, including definitions, will control.

The compositions of the present invention include a multiplicity of coated microgranules, which comprise moguisteine with one or more optional plasticizers and excipients, to which at least three successive layers of polymeric coatings are applied, at least one of the coatings imparting controlled-release characteristics to formulations containing the coated microgranulates. Three sequential coatings preferably comprise (i) cellulose acetate phthalate and plasticizer(s); (ii) one or more waxes; and (iii) cellulose acetate phthalate, respectively. (The coating (iii) can be identical to coating (i).) The coated microgranules are then formulated for use in liquid suspensions.

These formulations preserve the release characteristics of the dosage forms carried in them. They can be designed either as ready-to-use and time-stable liquid formulations with a shelf-life of at least two years, or as dry formulations that are reconstituted with water when needed and then remain stable throughout the treatment period.

The present invention provides a controlled-release pharmaceutical composition that includes: coated microgranules for the controlled release of moguisteine having sizes ranging from 50 to 500 μm, preferably from 90 to 300 μm, which are capable of remaining easily in suspension in a liquid for extended times. The microgranules comprise:

a) A core of moguisteine, with one or more optional plasticizers and excipients, granulated into microgranules having sizes smaller than 500 μm, uniform surfaces, substantially spherical shapes, apparent densities of about 500 to 600 g/l and very low friabilities, which are obtained by wet-kneading micronised moguisteine (and plasticizers and excipients if present), using water or a mixture of water and other solvents. This results in microgranules with no controlled-release properties prior to coating, which have physical properties that ensure reproducible and uniform distribution of subsequent coating layers.

b) A first coating having essentially hydrophilic characteristics, which isolates the microgranules.

c) A second coating having lipophilic characteristics on top of the first coating.

d) A third coating having hydrophilic characteristics.

Also provided is a vehicle system for the above controlled-release forms, comprising either a dry mixture of additives which can be combined with the microgranules for long-term drug storage, or an aqueous solution with optional additives in which the moguisteine-containing microgranules can be suspended and maintained in optimum release conditions for an extended period of time. Non-limiting examples of the additives are given below.

The elements that comprise the pharmaceutical formulations of the present invention are described below without limitation:

Microgranular Core

Microgranules with a high moguisteine content and appropriate physical properties (including size, shape, density and friability) that ensure uniform coating and suspendability are formed by wet-kneading a microgranular mixture comprising moguisteine. Procedures for mixing may be as described in U.S. Pat. No. 5,296,236, or as described in co-pending U.S. patent application Ser. No. 08/188,193 (the "'193 application", now U.S. Pat. No. 5,460,828.

In a preferred embodiment, polyethylene glycol, (available as Carbowax from BASF Corp., Parsippany, N.J.) is added to the microgranulate mixture before kneading, in an mount from about 0.3 to about 1%, preferably 0.6%, relative to the weight of the mixture, to promote an optimum spherical shape and surface smoothness of the microgranules to be coated. PEG is highly soluble in water (i.e., at concentrations higher than 10% W/V) and thus facilitates wetting of moguisteine, which is relatively insoluble in aqueous fluids. PEG was surprisingly found to promote the formation of microgranule spherical shapes even when present at concentrations lower than 1%. In practicing the present invention, any PEG preparation containing polymers of molecular weight from 200 to 8000 may be used, preferably from 5000 to 7000, and most preferably PEG 6000 (CARBOWAX® 6000).

The moguisteine-containing microgranular cores may also contain optional excipients, including fillers and binders, selected without limitation from those commonly used in wet mixing, such as lactose, dibasic calcium phosphate, microcrystalline cellulose, starch, talc, sugars, polyvinylpyrrolidone, gelatin, a copolymer of polyvinylpyrrolidone and vinyl acetate, and the like. Preferably, the microgranules contain lactose as a filler (lactose content is in the range 10-50% by weight) and polyvinylpyrrolidone as a binder (PVP content is in the range 5-20% by weight).

Procedures for mixing may be as described in the '236 patent, or as described in the '193 application. The mixing liquid used for wet-granulation, for example in high-speed mixer-granulators, can be water; or a solvent that is miscible with water, such as, for example, ethyl alcohol or other alcohols used in the pharmaceutical industry; or mixtures of water and at least one other solvent thereof.

The operating conditions for the kneading and granulation steps are those that result in a microgranulate with optimum physical characteristics that enable the deposition of an effective coating. For example, the '193 application describes acceptable and preferred ranges for process parameters using a fast mixer and mill, e.g., the relative proportion of mixing fluid added to the dry microgranulate mixture; the rate at which the fluid is sprayed; the spray pressure; the kneading time; and the independent mixer and mill speeds. The kneaded mixture is then dried to a residual humidity of 1-10%, preferably 5-8%, and screened to select particles of the required size range. Finally, the resulting microgranulate is evaluated with respect to the following properties: particle size distribution, density (aerated, packed, and apparent), Carr index (compressibility), and angle of repose. Finally, as described below, the granulate is coated with films of different compositions.

Coatings

Coating the moguisteine-containing microgranulate in accordance with the present invention serves at least two purposes. First, the coatings prevent the release of moguisteine in the oral cavity, thereby masking the bitter taste of moguisteine and increasing the palatability of liquid formulations comprising moguisteine. Second, the coatings ensure a controlled-release profile of moguisteine delivery after it reaches the gastric and intestinal milieus. Coated moguisteine-containing microgranules should comprise a pH-resistant (i.e., enteric) coating layer but it need not be the first one applied of the at least three coatings. Moguisteine-containing microgranules are thus coated with at least three alternating hydrophilic and hydrophobic coating layers as described below. Preferably, the last-applied coating should be hydrophilic to aid solvation and suspension. The preferred coating technique for all of the coating below, is the fluid-bed technique in accordance with the Wuster technology (Jones, D., *Drug Dev.Indus.Pharm.* 20:3175-3206, 1994).

Substances suitable for the first type of coating include without limitation hydrophilic substances such as, for example, derivatives of cellulose (such as cellulose acetate phthalate, hydroxypropylmethyl cellulose phthalate, ethyl cellulose, carboxyl methyl cellulose acetate, and the like) and acrylic polymers (such as co-polymers of esters of methacrylic and acrylic acid, methyl methacrylate, and the like). Preferably, cellulose acetate phthalate or hydroxypropylmethylcellulose phthalate are used. These polymers may be optionally mixed with plasticizers such as diethyl phthalate, dibutyl sebacate, vegetable oils and the like that are well-known in controlled-release formulations.

Substances suitable for the second type of coating layer, which has a lipophilic nature, include without limitation fatty substances such as mono-, di- and tri-glycerides of $C_6$–$C_{36}$ fatty acids, carnauba wax, beeswax, candelilla wax, alcohols, fatty acids and combination thereof. These coatings can be applied with the help of chlorinated solvents. Preferably, however, the waxes are applied in the melted state, with no use of solvents. Since moguisteine has a low melting point (65° C.), it is important to use conditions that allow coating without melting the moguisteine in the core. It has now been found that the use of a coaxial nozzle, wherein the spray fluid is compressed air that is sufficiently heated to maintain the waxes constantly in the liquid state, as well as maintenance of the temperature of the coating chamber sufficiently warm, allows the waxes to coat a moguisteine-containing microgranulate without melting the moguisteine.

The same substances that make up the first coating layer may also be used for the third coating layer. It is in any event preferred that the last-applied coating be hydrophilic, as stated above.

Vehicle

In practicing the present invention, the moguisteine-containing microgranulate, coated according to the above procedures, is combined with a vehicle to form either a dry mixture that can be suspended extempore when needed, or a ready-to-use liquid suspension.

For addition to the coated microgranules comprising controlled-release dosage forms of moguisteine, the constituents of the vehicle can include without limitation:

- suspending or structuring agents such as cellulose esters, microcrystalline cellulose, alginic acid derivatives, and polyvinylpyrrolidone derivatives;
- surfactants (preferably anionic or nonionic) such as Span 20, Span 80, Tween 20, and sodium lauryl sulfate;
- sugars such as sucrose, sorbitol, xylitol, dextrose and the like;
- buffering substances such as citric acid and sodium citrate, glycine and hydrochloric acid, sodium phosphate, and potassium phosphate;
- preservatives and bacteriostatic agents such as esters of p-hydroxybenzoic acid; and
- various flavorings and sweeteners commonly used in pharmaceuticals.

It will be understood that the specific composition of the formulation, with respect to both nature and amount of added ingredients, will vary according to the particular application. See, e.g., Wade and Weller, eds., *Handbook of Pharmaceutical Excipients* (2d. Ed.), The Pharmaceutical Press, London, 1994.

In addition to the above ingredients, the ready-to-use formulation also comprises water, or mixtures of water and pharmaceutically acceptable water-miscible co-solvents known in the art such as glycols, alcohols and glycerol.

The compositions of the present invention lend themselves to different presentation forms, including, for instance, (i) multi-dose granular formulations wherein dose flexibility is obtained by measuring different amounts of granules to be re-suspended when needed; (ii) accurately-measurable single-dose formulations in the form of sachets; (iii) bottles with reservoir caps for offhand reconstitution; and other forms known to the art. For pediatric use, the present invention also encompasses formulations comprising concentrated drops (e.g., drops containing 10% w/v moguisteine which works out to about 5 mg of active ingredient per drop) in which the granules containing moguisteine are suspended.

Therapeutic Administration

The pharmaceutical formulation of the present invention are intended to deliver effective amounts of moguisteine in one or two daily administrations. An "effective amount" of moguisteine is one that provides relief from coughing in a patient. It will be understood that an effective amount can be delivered at a given time by ingestion of a single dose or a plurality of doses. Typically, a daily dose of moguisteine effective in preventing and/or treating coughing is from about 5 to about 15 mg/kg weight of the patient. The average dose is 9 mg/kg. Thus, administration of an antitussive effective amount of moguisteine may involve once or twice daily administration of about 2 to about 30 ml and preferably 10 ml of a final formulation (prepared as described in Example 8A below) containing 30 mg/ml moguisteine.

The benefits of the present invention include a considerable improvement in patient compliance, based on both a reduction in the number of daily doses and good palatability. Additional benefits are anticipated in pediatric practice due to the ease of administration and swallowing. Furthermore, a better therapeutic response is likely to result, since, in a preferred embodiment, the formulation permits modulation of dosage as a function of need simply by measuring the required suspension volumes.

The examples provided below are intended to more fully describe preferred embodiments of the invention and to demonstrate its advantages and applicability, without limiting its scope.

EXAMPLE 1

Preparation of a Moguisteine Microgranulate

A mixture made up of 79% (w/w) moguisteine, 10% (w/w) polyvinylpyrrolidone (PVP K30) and 10% (w/w) 450-mesh lactose was mixed in a Diosna P25 mixer-granulator for 10 minutes. A 1% (w/w) of PEG 6000 was added as an aqueous solution to the stirred mixture at a rate of 25 ml/min using a 0.8 mm nozzle at a pressure of 2 bars. During the wetting step the mixer speed was 175 rpm and the speed of the mill was 3000 rpm. The time required to add the solution was 20 minutes. After wetting, the kneading and rounding step was performed by maintaining mixer and mill speeds at a constant rate for 15 minutes. The microgranulate so obtained was dried in an artificial-ventilation incubator and then sieved through a 225-mesh/$cm^2$ screen until a microgranulate with a granule size distribution ranging from 90 to 300 μm, a spheroidal shape, a tapped density of 0.593 g/ml, and a real density of 1.36 g/ml was obtained.

EXAMPLE 2

A mixture made up of 79.4% (w/w) moguisteine, 10% (w/w) lactose, 10% (w/w) PVP K30 and 0.6% PEG 6000 was mixed and kneaded as in Example 1.

EXAMPLE 3

A mixture made up of 79.4% (w/w) moguisteine, 10% (w/w) 450-mesh lactose, 10% (w/w) PVP K30 and 0.6% (w/w) PEG 6000 was wetted with 500 ml of water, which was added at a rate of 25 ml/min over 15 minutes. PEG was added as a 5% solution as in Example 1 above. The speed of the mixer was 175 rpm and that of the mill 3000 rpm. The microgranulate obtained after drying had 4% residual moisture, an untapped density of 0.548 g/ml, a tapped density of 0.669 g/ml, a Carr index of 18.08% and an actual density of 1.38 g/ml. The above parameters are described in detail in Ellis Horwood, Ed., (1988), *Pharmaceutical Preformulation*, pp. 209–214, Chichester, England; and in *Advances in Pharmaceutical Science;* 2:181–220, 1967. Individual particles within the microgranulate thus obtained exhibited a particular surface smoothness due to the presence of PEG 6000.

EXAMPLE 4

First Film Layer (Cellulose Acetate Phthalate)

Two kg of the microgranulate prepared in accordance with Example 3 were stirred for 1 minute in a Glatt GPCG3 (Glad, GmbH, Buizen Lorrach, Germany) fluidizer into which air heated at a temperature of 40° to 45° C. was blown at a rate of 40 $m^3$/hour. The granulate was sprayed at a pressure of 2 bars and a rate of 10 to 13 g/min with 400 ml of a solution having the following weight percent composition:

| | |
|---|---|
| Cellulose acetate phthalate | 4% |
| Diethyl phthalate | 1% |
| Acetone | 71% |
| Isopropyl alcohol | 24% |

EXAMPLE 5

Second Film Layer (Waxes)

A solution having the following weight percent composition was prepared:

| | |
|---|---|
| Glyceryl monostearate | 4.50% |
| White beeswax | 0.40% |
| Cetyl alcohol | 0.05% |
| Stearyl alcohol | 0.05% |
| Chloroform | 90.60% |
| Methanol | 4.40% |

1.152 g of this solution were applied to 2000 g of the microgranulate previously coated with a first layer as described in Example 4. The identical operating conditions as in Example 4 for apply the second layer were used in this case.

EXAMPLE 6

A mixture of waxes was prepared having the following weight percent composition:

| | |
|---|---|
| Glyceryl monostearate | 90% |
| White beeswax | 8% |
| Cetyl alcohol | 1% |
| Stearyl alcohol | 1% |

This mixture was applied in the melted state to microgranules previously coated with a first layer as described in Example 4. In this case, the waxes were first melted by incubation at a temperature of about 110° C. They were then sprayed in the melted state at a temperature of about 80° C., onto 2 kg of microgranulate. This was accomplished using air pre-heated at a temperature of 125° C. and compressed to a pressure of 3 bars using a coaxial nozzle which mixes the melted wax and the hot compressed air. The spraying step was performed with a 7" Wurster insert in a Glatt apparatus. Wax amounts equivalent to 3.8% by weight (relative to the weight of the uncoated microgranulate) were sprayed at a rate of about 1.5 g/min.

EXAMPLE 7

Third Film Layer

The same ingredients and procedures described in Example 4 for depositing the first coating layer were used for the final coating layer.

EXAMPLE 8

Pharmaceutical Formulations Comprising Moguisteine

A) Suspension in multi-dose bottles

A microgranulate, prepared as described in Example 3 and coated with three successive layers as described in Example 4, 5 and 7, was added to a final proportion of 12.5% (w/w) to a mixture containing 6.2% microcrystalline cellulose, 0.8% sodium carboxymethylcellulose, 0.5% sodium citrate, 0.8% citric acid, 0.2% methylparaben, 0.05% propylparaben, 2% tragacanth, 0.05% Span 20 surfactant, 0.2% dimethylpolysiloxane, 0.01% glycamil, 0.25% orange-grapefruit flavor and powdered sugar to 100%. (The above values all represent percentages by weight.) By adding 80 g of water to 33 g of suspension mixture, a 100 ml suspension containing 30 mg/ml of moguisteine was obtained. The parabens in the foregoing formulation serve as preservatives; dimethylpolysiloxane is an anti-foam agent.

B) Suspension in single-dose packages 3.3 g of a suspension mixture prepared as described at paragraph A were divided into individual aliquots, each comprising a single 300 mg dose of moguisteine, in paper/aluminum/polythene packages. The contents of each package may be re-suspended in half a glass of water.

C) Suspension in single-dose bottles 1.25 g of a microgranulate, prepared as described in Example 3 and coated successively as described in Example 4, 5 and 7, were placed in the reservoir cap of a single-dose bottle (Bormioli Metalplast, Parma, Italy) and kept separate from the liquid contained in the single-dose bottle. The composition of the single dose was 3,500 mg of 70% sorbitol, 15 mg of pineapple-lemon flavors, 15 mg of citric acid, 10 mg of sodium benzoate, and purified water to 8 ml. Before use, the contents of the reservoir cap are put in contact with the liquid in the bottle by pressing the reservoir cap. Each bottle contains 300 mg of moguisteine as a single-dose suspension.

D) Ready-to-use suspension

To obtain 100 ml of a ready-to-use suspension, 4 g of a microgranulate that had been prepared as described in Example 3 and coated with three successive layers as described in Examples 4, 5, and 6, respectively, were added slowly and under vacuum to a liquid vehicle having the following composition:

| | |
|---|---|
| cellulose (microcrystalline) | 0.85 g |
| sodium carboxymethylcellulose | 0.15 |
| sodium lauryl sulfate | 0.10 |
| potassium sorbate | 0.15 |
| sorbitol (70% solution) | 67.50 |
| glycerin | 11.80 |
| xanthan gum | 0.12 |
| titanium dioxide | 0.50 |
| dimethylpolysiloxane | 0.10 |
| citric acid monohydrate | 0.10 |
| mannitol | 0.40 |
| flavor | 0.15 |
| purified water | to 100 ml |

This solution requires no further reconstitution, but can be used by the patient directly as is.

EXAMPLE 9

In Vitro Testing of Release

Release of moguisteine from coated microgranules prepared as described in Examples 3, 4, 5 and 7 was tested using apparatus II (paddle) described in the United States Pharmacopoeia Ed. XXII, operating at 75 rpm at 37° C. 900 ml of dissolution medium were used for 300 mg of moguisteine. For the first hour, the dissolution medium was 0.1 N HCl and, from the second to the twelfth hours, phosphate buffer at pH 7.4. The amount of active ingredient released into solution was determined spectrophotometrically by measuring absorbance of the solution at 275 μm. The percentages of active ingredient released in time (hours) by a microgranulate were as follows: 21% (1 hour), 46% (2 hours), 78% (4 hours), 93% (8 hours) and 98% (12 hours).

EXAMPLE 10

Testing of Dissolution Stability with Time

A) The stability of a controlled-release suspension prepared as described in Example 8, Section A was determined in the following manner. The coated microgranulate and drug vehicle component mixture was reconstituted in water initially, at 3 months, and 6 months, and the in vitro release of moguisteine was tested using the procedure described in Example 9. The results are shown in Table 1:

TABLE 1

| Stability conditions | % of moguisteine released | | | | |
|---|---|---|---|---|---|
| | 1h | 2h | 4h | 8h | 12h |
| Initial | 22 | 50 | 77 | 94 | 95 |
| 25° C., 3 months | 21 | 52 | 82 | 97 | 98 |
| 25° C., 6 months | 22 | 52 | 80 | 95 | 96 |
| 35° C., 6 months | 22 | 50 | 76 | 89 | 90 |

These data demonstrate that the release profile for moguisteine was essentially unchanged even for samples that were reconstituted after storage for 6 months at 35° C.

In another test involving an identical formulation, the dissolution profile of the suspension was evaluated 15 days after reconstitution with water. The results are shown in Table 2.

TABLE 2

| Dissolution conditions | % of moguisteine released | | | | |
|---|---|---|---|---|---|
| | 1h | 2h | 4h | 8h | 12h |
| Initial | 22 | 50 | 77 | 94 | 95 |
| After 15 days | 21 | 48 | 79 | 93 | 95 |

The dissolution profile of moguisteine was unchanged even 15 days after reconstitution with water, thus ensuring good dissolution stability throughout a typical course of therapy.

B) The stability of a controlled release ready-to-use suspension prepared as described in Example 8, Section D was determined as described above by assessing the percentage of moguisteine release initially and after 18 months. The results are shown in Table 3.

TABLE 3

| Dissolution | % of moguisteine released | | | | |
|---|---|---|---|---|---|
| | 1h | 2h | 4h | 8h | 12h |
| Initial | 18 | 48 | 76 | 97 | 100 |
| After 18 months | 19 | 50 | 76 | 93 | 98 |

In this ready-to-use formulation, the dissolution profile of moguisteine was unchanged after 18 months; this is presumably due to the relatively low proportion of water in the formulation (approximately 30%).

EXAMPLE 11

Physical Characteristics of Moguisteine Formulations

Water up to 100 ml was added to 33 g of a suspension prepared as described in Example 8. The following parameters were then measured: 1) Sedimentation F, which is the ratio between the height of the sediment the height of a suspension that had been stirred allowed to st for 3 days; 2) pH; 3) viscosity, as measured with a Brookfield DVII apparatus; 4) density. The results were as follows: F=0.6, pH=4.3, Viscosity (cps)=226, and Density (g/ml)=1.1.

EXAMPLE 12

Bioavailability

A single-dose kinetic study using the formulation of the present invention was conducted to evaluate moguisteine bioavailability. Six healthy volunteers received a single 10 ml dose of a controlled-release liquid formulation (equivalent to 300 mg of moguisteine) prepared as described in Example 8. Blood samples were taken at different times, and the moguisteine plasma concentration (evaluated as an acid) was determined by an HPLC method. In a second trial, the volunteers were administered a dose of a conventional 2% suspension equivalent to 200 mg of moguisteine. Table 4 compares the main pharmacokinetic parameters obtained from the two formulations.

TABLE 4

| Moguisteine | Cmax (μg/ml) | Tmax h | AUC (μg h/ml) |
|---|---|---|---|
| C.R. suspension | 1.79 | 2.83 | 7.05 |
| Standard suspension | 3.05 | 0.73 | 4.01 |

$C_{max}$ = (Peak concentration): the highest plasma concentration the drug reaches after the administration;
$T_{max}$ = (Time concentration) the time necessary to reach the $C_{max}$ value;
$AUC_{0-\infty}$ = (Area under the curve) the total area of the time-concentration profile and represents a measure of the bioavailability.

These data indicate that in the controlled-release formulation of the present invention:

(a) $T_{max}$ is delayed and $C_{max}$ is reduced relative to the conventional suspension, as expected for a controlled-release formulation;

(b) The half-life ($t_{1/2}$) and the calculated mean residual time (MRT) are increased three-fold relative to the conventional suspension; and (c) The AUC and, accordingly, the relative bioavailability are similar to the conventional suspension.

These data indicate that the suspension prepared according to the present invention exhibits the properties of a controlled release formulation with excellent bioavailability.

FIG. 1 shows these results after normalization of moguisteine blood levels for the difference between the initial moguisteine dose in the controlled-release and conventional formulations. The graph shows dose concentration values ($L^{-1}$) on the ordinates and time on the abscissas. The data indicate that the administration of moguisteine according to the present invention permits the initial peak effect to be avoided and the number of daily dosages to be reduced, while ensuring satisfactory therapeutic blood levels of moguisteine over an extended time.

FIG. 2 shows a simulation of blood levels of moguisteine after two administrations of a standard suspension or a single administration of the controlled-release suspension. The controlled-release suspension avoids the initial peak effect (thus minimizing associated side effects) observed with the standard suspension. Furthermore, the controlled-release suspension can be used in a twice-daily administration regimen, versus four times daily with the standard suspension.

What is claimed is:

1. A controlled-release pharmaceutical dosage form suitable for the administration of moguisteine in a liquid suspension, which controlled-release pharmaceutical dosage form comprises:

microgranules containing moguisteine as an active ingredient, said microgranules before being coated having a smooth surface and substantially spherical shape and no controlled-release properties, said microgranules comprising a plurality of at least three coatings thereon, at least one of said coatings imparting controlled release properties to said microgranules, the first of said coatings thereon being pH sensitive, said at least three coatings comprising alternating hydrophilic and lipophilic layers applied to said microgranules, said coatings preventing tastable dissolution of said moguisteine upon ingestion and ensuring a predetermined sustained release profile of moguisteine and maintenance over time of said release profile, said lipophilic layer being free of organic solvent, wherein said dosage form when ingested does not result in immediately bioavailable extragranular moguisteine being released into the oral cavity.

2. The dosage form of claim 1 further comprising a vehicle for the administration of said coated microgranules.

3. The dosage form of claim 2, wherein said vehicle comprises one or more agents selected from the same consisting of suspending, structuring, surfactant, sweetening, buffering, preserving, and flavoring agents and combinations of at least two of the foregoing.

4. The dosage form of claim 2, further comprising water, or mixtures of water and pharmaceutically acceptable water-miscible co-solvents selected from the group consisting of glycols, alcohols and glycerol.

5. The dosage form of claim 1, wherein said plasticizer comprises polyethylene glycol.

6. The dosage form of claim 5, wherein said excipient comprises a compound selected from the group consisting of polyvinylpyrrolidone, lactose, dibasic calcium phosphate, microcrystalline cellulose, starch, talc, sugars, a polyvinylpyrrolidone / vinyl-acetate copolymer and gelatin.

7. The dosage form of claim 5, wherein said polyethylene glycol is present in said microgranules at a level of 0.5 to 1% by weight as compared to the total dry weight of the microgranules.

8. The dosage form of claim 1, wherein said hydrophilic coating comprises polymers selected from the group consisting of cellulose acetate phthalate and hydroxypropylmethylcellulose phthalate.

9. The dosage form of claim 8, wherein said hydrophilic coating further comprises a plasticizer selected from the group consisting of diethyl phthalate, dibutyl sebacate and vegetable oils.

10. The dosage form of claim 9, wherein said plasticizer comprises from 10 to 30% by weight of the total weight of said hydrophilic layer.

11. The dosage form of claim 1, wherein said lipophilic coating comprises a waxy material selected from the group consisting of mono-, di- tri-glycerides of $C_6$–$C_{36}$ fatty acids, carnauba wax, beeswax, candelilla wax, alcohols, fatty acids, and combinations thereof.

12. The dosage form of claim 11, wherein said waxy material is applied in its melted state using heated compressed air as a spray medium.

13. A method for symptomatic treatment of coughing, which comprises administering antitussive effective amounts of the dosage form of claim 1.

14. The dosage form of claim 1, wherein said microgranules further comprise a plasticizer and excipient.

15. A controlled release pharmaceutical dosage form suitable for the administration of moguisteine in a liquid suspension, which comprises:

microgranules containing moguisteine as an active ingredient and polyethylene glycol as a plasticizer, said microgranules before coating having a smooth surface and substantially spherical shape and no controlled-release properties, said microgranules comprising a plurality of at least three coatings thereon, at least one of said coatings imparting controlled-release properties to said microgranules, wherein a first one of said coatings comprises cellulose acetate phthalate, a second one of said coatings applied successively on said first coating comprises a mixture of glyceryl monostearate and beeswax, and a third of said coatings applied successively on said second coating comprises cellulose acetate phthalate, said first coating being pH sensitive, said second coating being free of organic solvent, said coatings preventing tastable dissolution of said moguisteine upon ingestion and ensuring a predetermined sustained release profile of moguisteine and maintenance of said release profile, wherein said dosage form when ingested does not result in immediate bioavailable extragranular moguisteine being released into the oral cavity.

16. The dosage form of claim 15, further comprising a vehicle for the administration of said coated microgranules.

17. The dosage form of claim 15, wherein said polyethylene glycol is PEG 6000.

18. A method for preparing a palatable controlled-release pharmaceutical dosage form for the administration of moguisteine in a liquid suspension, which comprises:

(a) mixing moguisteine and at least one plasticizer to form micro-granules; and (b) coating the microgranules with a first, hydrophilic, coating layer comprising a polymer selected from the group consisting of cellulose acetate phthalate and hydroxypropylmethylcellulose phthalate and combinations thereof, said first coating being pH sensitive;

(c) coating the microgranules formed in (b) with a second, lipophilic, coating comprising a waxy material selected from the group of mono-, di- tri-glycerides of $C_6$–$C_{36}$ fatty acids, carnauba wax, beeswax, and candelilla wax, alcohols, fatty acids, and combinations thereof, wherein said waxy material is applied in its melted state using heated compressed air as a spray medium, said second coating being free of organic solvent; and (d) coating the microgranules formed in (c) with a third, hydrophilic coating comprising a polymer selected from the group consisting of cellulose acetate phthalate and hydroxypropylmethylcellulose phthalate and combinations thereof.

19. A composition for use in the symptomatic treatment of coughing, said composition comprising:

microgranules containing moguisteine as an active ingredient, said microgranules before being coated having a smooth surface and substantially spherical shape and no controlled-release properties, said microgranules comprising a plurality of at least three coatings thereon, at least one of said coatings imparting controlled release properties to said microgranules, the fist of said coatings thereon being pH sensitive, said at least three coatings comprising alternating hydrophilic and lipophilic layers applied to said microgranules, said coatings preventing tastable dissolution of said moguisteine upon ingestion and ensuring a predetermined sustained release profile of moguisteine and maintenance over time of said release profile, said lipophilic layer being free of organic solvent, wherein the composition when ingested does not result in immediately bioavailable moguisteine being released into the oral cavity.

20. The composition of claim 19 further comprising a vehicle for the administration of said coated microgranules.

21. The composition of claim 20, wherein said vehicle comprises one or more agents selected from the same consisting of suspending, structuring, surfactant sweetening, buffering, preserving, and flavoring agents and combinations of at least two of the foregoing.

22. The composition of claim 21, further comprising water, or mixtures of water and pharmaceutically acceptable water-miscible co-solvents selected from the group consisting of glycols, alcohols and glycerol.

23. The composition of claim 19, wherein said plasticizer comprises polyethylene glycol.

24. The composition of claim 23, wherein said polyethylene glycol is present in said microgranules at a level of 0.5 to 1% by weight as compared to the total dry weight of the microgranules.

25. The composition of claim 19, wherein said excipient comprises a compound selected from the group consisting of polyvinylpyrrolidone, lactose, dibasic calcium phosphate, microcrystalline cellulose, starch, talc, sugars, a polyvinylpyrrolidone/vinyl-acetate copolymer and gelatin.

26. The composition of claim 19, wherein said hydrophilic coating comprises polymers selected from the group consisting of cellulose acetate phthalate and hydroxypropylmethylcellulose phthalate.

27. The composition of claim 26, wherein said hydrophilic coating further comprises a plasticizer selected from the group consisting of diethyl phthalate, dibutyl sebacate and vegetable oils.

28. The composition of claim 27, wherein said plasticizer comprises from 10 to 30% by weight of the total weight of said hydrophilic layer.

29. The composition of claim 19, wherein said lipophilic coating comprises a waxy material selected from the group consisting of mono-, di- tri-glycerides of $C_6$–$C_{36}$ fatty acids, carnauba wax, beeswax, candelilla wax, alcohols, fatty acids, and combinations thereof.

30. The composition of claim 29, wherein said waxy material is applied in its melted state using heated compressed air as a spray medium.

31. The composition of claim 19, wherein said microgranules further comprise a plasticizer and excipient.

32. A composition for use in the symptomatic treatment of coughing, said composition comprising:

microgranules containing moguisteine as an active ingredient and polyethylene glycol as a plasticizer, said microgranules before coating having a smooth surface and substantially spherical shape and no controlled-release properties, said microgranules comprising a plurality of at least three coatings thereon, at least one of said coatings imparting controlled-release properties to said microgranules, the first of said coatings thereon being pH sensitive, a first one of said coatings comprising cellulose acetate phthalate, a second one of said coatings applied successively on said first coating comprising a mixture of glyceryl monostearate and beeswax, and a third one of said coatings applied successively on said second coating comprising cellulose acetate phthalate, said coatings preventing testable dissolution of said moguisteine upon ingestion and ensuring a predetermined sustained release profile of moguisteine and maintenance of said release profile, said second coating being free of organic solvent; and a vehicle for the administration of said coated microgranules, wherein said composition when ingested does not result in immediately bioavailable extragranular moguisteine being released into the oral cavity.

33. The composition of claim 32 wherein said polyethylene glycol is PEG 6000.

34. A controlled-release pharmaceutical dosage form suitable for the administration of moguisteine in a liquid suspension, which comprises:

microgranules containing moguisteine as an active ingredient, said microgranules before being coated having a smooth surface and substantially spherical shape and no controlled-release properties, said microgranules comprising a plurality of at least three coatings thereon, at least one of said coatings imparting controlled release properties to said microgranules, said at least three coatings comprising alternating hydrophilic and lipophilic layers applied to said microgranules, said coatings preventing tastable dissolution of said moguisteine upon ingestion and ensuring a predetermined sustained release profile of moguisteine and maintenance over time of said release profile, at least one of said lipophilic layers comprising a waxy material selected from the group of mono-, di- tri-glycerides of $C_6$–$C_{36}$ fatty acids, carnauba wax, beeswax, and candelilla wax, alcohols, and fatty acids, wherein said waxy material is free of organic solvents.

* * * * *